(12) United States Patent  
Islava

(10) Patent No.: US 6,666,836 B1
(45) Date of Patent: Dec. 23, 2003

(54) THERMAL TREATMENT SYSTEM

(75) Inventor: Steve T. Islava, San Clemente, CA (US)

(73) Assignee: STI Medical Products, Inc., Costa Mesa, CA (US)

( * ) Notice: Subject to any disclaimer, the term of this patent is extended or adjusted under 35 U.S.C. 154(b) by 0 days.

(21) Appl. No.: 09/827,468

(22) Filed: Apr. 6, 2001

(51) Int. Cl.[7] ................................................ A61F 5/00
(52) U.S. Cl. .............................. 602/2; 602/41; 607/96
(58) Field of Search ............................. 602/2, 14, 41; 607/96, 108, 112, 114

(56) References Cited

U.S. PATENT DOCUMENTS

| | | | |
|---|---|---|---|
| 3,871,376 A | 3/1975 | Kozak | 128/275.1 |
| 4,377,161 A | 3/1983 | Whitt | 128/200.24 |
| 4,517,972 A | 5/1985 | Finch, Jr. | 128/156 |
| 4,556,055 A | 12/1985 | Bonner, Jr. | 128/82.1 |
| 4,854,319 A | 8/1989 | Tobin | 128/380 |
| 4,981,135 A * | 1/1991 | Hardy | 602/2 |
| 5,702,375 A * | 12/1997 | Angelillo et al. | 602/2 |
| 5,913,849 A | 6/1999 | Sundstrom et al. | 604/291 |
| 5,984,951 A | 11/1999 | Weiss et al. | 607/109 |
| 6,017,606 A | 1/2000 | Sage et al. | 428/68 |
| 6,068,607 A * | 5/2000 | Palmer et al. | 607/112 |
| 6,269,654 B1 * | 8/2001 | Murray et al. | 62/530 |
| 6,348,212 B2 * | 2/2002 | Hymes et al. | 424/449 |

* cited by examiner

Primary Examiner—Michael A. Brown
(74) Attorney, Agent, or Firm—Reed Smith Crosby Heafey

(57) ABSTRACT

An improved device for attaching thermal dressings—using essentially any type of source of heat or cold employs a novel adhesive that permits firm attachment of the dressing to essentially any portion of the human anatomy with no need for wrapping around the limb or other anatomical region. The adhesive is sufficiently weak that the dressing can be peeled from the skin—even in the presence of body hair—with no pain. The adhesive, a hypoallergenic hydrophilic gel, is thick and soft and adheres by molding itself to the skin surface, and into and around hair shafts. The material contains essentially no elastomers and does not grip hair or pull strongly on hairs when the dressing is removed. When the gel becomes dehydrated, it loses most, if not all, of its adhesive properties. The gel is sufficiently crosslinked so as to resist dissolution by additional water.

12 Claims, 6 Drawing Sheets

THERMAL TREATMENT SYSTEM

BACKGROUND OF THE INVENTION

1. Area of the Art

The present invention concerns the field of medical treatments and more specifically a system for removably attaching a source of heat or cold to a human body.

2. Description of the Prior Art

Most people are almost inherently aware of the medical benefits of local application of either heat or cold. In many cases thermal treatments can have almost miraculous results that surpass those provided by many complex and expensive pharmaceutical agents.

When joints and muscles are traumatized as in a sprain or similar injury, there is great benefit to the rapid application of cold to the site of injury. The lowering of temperature inhibits the inflammatory processes that can actually exacerbate the injury if allowed to run out of control. Low temperatures inhibit the movement and penetration of white blood cells that mediate inflammation. Low temperatures also inhibit the cellular responses to inflammatory molecules that are released at the site of injury.

Other medical problems such as migraine headache also respond favorably to application of cold. In some cases colds is mostly anaesthetic acting by inhibiting conduction of pain signals through the nerves. In many other cases as discussed for traumatic injury the cold is more than palliative. Paradoxically many conditions, including the injuries that are initially benefited by application of reduced temperatures, are later benefited by application of heat. Whereas cold dulls the extreme pain of traumatic injury, heat alleviates chronic pain particularly of joint origin. The explanations for the positive effects of applied heat are, perhaps, even more obscure than those for the application of cold. Generally, applied heat increases the local blood flow. In some cases increased blood flow may be essential for or stimulate tissue regeneration and healing. Much chronic pain is caused by muscle spasms and the like. Applied heat often results in muscle relaxation and a diminution of spasms.

Because of the benefits of thermal manipulation—that is applied heat or cold, there have been a plethora of devices intended to manipulate the thermal status of portions of the human body. Some of these have been fairly complex such as diathermy instruments and related devices that cause localized heating mediated by the application of sonic or electromagnetic energy to the body. However, the majority of such devices have been means to attach a portable source of heat or cold to some portion of the body. Generally, these devices consist of some combination of straps, catches and hook-in-loop fasteners to removably attach a hot or cold pack to some portion of the body. In some cases direct adhesives have been used but there has been a continuing problem with the removal of such adhesive attached thermal treatments. Their removal can damage the skin, or if they are placed over a region having significant body hair, their removal can be painful indeed. In a hospital situation a variety of different solvents may be used to help remove the adhesives, but this is often safe neither for the patient nor the environment.

U.S. Pat. No. 4,517,972 to Finch, Jr. illustrates a multi-purpose system for attaching thermal or other treatments. Essentially, the thermal treatment is removably attached by hook-in-loop fastener to patches of traditional adhesive. While this approach allows the ready removal or replacement of the thermal treatment, removal of the adhesive patches still involve the difficulties already mentioned. In particular the device cannot be attached to regions with abundant hair such as the male torso or even the crown of the head.

U.S. Pat. No. 3,871,376 to Kozak describes another thermal dressing employing layers of frozen hydrophilic gel to provide a cooling source. This structure is attached to the body with adhesives of the type "conventionally employed in the pressure-sensitive tape art". The thermal dressing disclosed in U.S. Pat. No. 5,702,375 to Angelillo et al. can be attached to the body by an optional region of "adhesive means".

Frequently in the prior art the thermal bandage or dressing is applied by means of wrapping (U.S. Pat. No. 4,377,160 to Romaine) or by means of a strap that wraps around a body portion and attaches to itself by means of a loop-in-hook fastener (U.S. Pat. No. 6,017,606 to Sage et al.; U.S. Pat. No. 5,984,951 to Weiss et al.; U.S. Pat. No. 4,854,319 to Tobin; U.S. Pat. No. 4,556,055 to Bonner, Jr.). This may be due to the problems with removing adhesive from or use of adhesive on hairy portions of the body. Further, many adhesives are adversely affected by the temperature extremes and/or wetness of thermal bandages.

U.S. Pat. No. 5,913,849 to Sundstrom et al. has attempted to deal with some of the shortcomings of ordinary adhesives by providing a special liquid-absorbing adhesive layer for use with heat dressings. The hydrogel adhesives of this disclosure are described as comprising discontinuous phases containing an elastomer and a resin. A discontinuous phase of water soluble/water swellable hydrocolloids are dispersed through out the continuous phase. It appears that the major motivation for use of this adhesive type is for treatment of exuding wounds wherein the adhesive absorbs the exuded fluid. Unfortunately, the latex or other elastomer employed is often hard to remove from the skin and can be irritating or allergenic.

SUMMARY OF THE INVENTION

The current invention is directed towards an improved means for attaching thermal dressings. A preferred embodiment is a device for ready attachment and removal of an "cold pack" wherein the cold is produced by one of the widely available salt/solvation devices. However, the present invention is operable using essentially any type of source of heat or cold. Ideally such a thermal source is self-contained and portable for use in first aid treatments; however, portability is not required. The present invention involves a novel adhesive that permits firm attachment of the dressing to essentially any portion of the human anatomy with no need for wrapping completely around the limb or other anatomical region. That is, the device attached to the skin with an adhesive that is sufficiently strong to maintain the device in position against repeated motion. Yet, the adhesive is sufficiently weak that the dressing can be peeled off from the skin—even in the presence of body hair—with essentially no pain.

These results are achieved using a hydrated gel adhesive with little or no intermixed elastomers or "traditional" adhesives as has been used with hydrated gels in the past. Because the adhesive is hydrophilic and relatively thick and soft, it adheres by molding itself to the skin surface, into irregularities and into and around hair shafts. However, because the material contains essentially no elastomers, it does not grip hair shafts and does not pull strongly on hairs when the dressing is peeled. Further, traditional elastomers contribute to the allergenic properties of the material. The relatively soft hydrophilic adhesive is essentially incapable of pulling on a hair. A traditional elastomeric adhesive attaches to a hair or to the skin by molding itself into crevices and various intricacies. When the adhesive is peeled off tiny bodies of elastomer remain within these crevices and tiny elastomeric bands stretch from the main dressing to these bodies. Ultimately these bans break under tension or the bodies are pulled from the crevices. In this process the skin surface or the hair is painfully tugged. The hydrophilic gel of the present invention adheres by molding itself to the surface, but when it is peeled away, the lack of elastomer causes it to cleanly detach with no painful tugging.

Because the hydrophilic gel adhesive of the present invention operates without a traditional elastomer, it's "sticking power" is essentially completely dependent on the ability of the gel to mold to a surface. If the gel becomes dehydrated, it loses most, if not all, of its power to stick. Therefore, it is necessary to supply the device of the current invention in an airtight impermeable package to maintain the gel adhesive in a hydrated state. Before use this package is opened and the adhesive surface is revealed by peeling back a protective covering similar to that of a normal adhesive bandage. The hydrophilic gel adhesive is preferably formed by coating a suitable gel on a backing of a felt-like non-woven fabric. The gel penetrates into the fabric which serves as a flexible support onto which the thermal portion of the dressing is attached by methods well known to the art. The ideal gel is essentially saturated with water and is sufficiently crosslinked so as to not be dissolved or washed away by additional water. That is, the gel can absorb a small amount of additional water—as from condensate of a cold pack—but the adhesive is not dissolved or washed away. Further, little or no adhesive transfers from the fabric backing to the skin or hair. Suitable gels include polysaccharide "gums" and polyacrylamides and similar acrylic derivatives. The gel can be coated onto the fabric using a suitable solvent which then evaporates leaving the gel permanently embedded in the fabric. Alternatively, the hydrophilic gel can be polymerized into the fabric from monomers. Ideally, the final product is a gel with little or no solubility in water at room temperature so that the gel remains attached to the fabric even if placed in water.

DETAILED DESCRIPTION OF THE INVENTION

Figure 1:
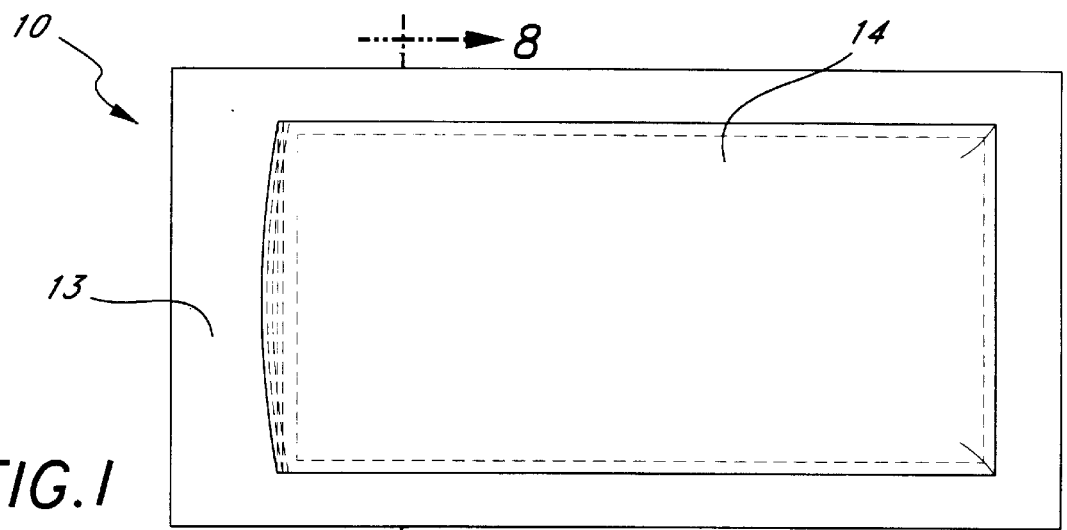
FIG. 1 shows a cold pack of the present invention as seen from above.

The following description is provided to enable any person skilled in the art to make and use the invention and sets forth the best modes contemplated by the inventor of carrying out his invention. Various modifications, however, will remain readily apparent to those skilled in the art, since the general principles of the present invention have been defined herein specifically to provide a dressing for removably adhering a thermal (hot or cold) dressing to a patient.

The present inventor has studied the various devices in use and has, concluded that many applications for thermal dressings are not readily adaptable to hook-in-loop straps and the like wherein the device must be wrapped completely around a body part for attachment. It is often the case that a thermal dressing needs to be applied to the patient's back or chest or some similar region where wrap around straps are not convenient. This is particularly true in treatment of medical emergencies where it may be desired to simply "slap" the dressing into position. This suggests that some type of adhesive is in order. However, it has already been mentioned that typical adhesives designed to adhere a bandage to a wound or even to close a wound are generally not suitable because they are painful to remove and are generally ineffective for use on hairy regions of the body. Further many of these "traditional" adhesives based on elastomers are not compatible with moisture as may be present as condensate from cold packs, etc. Generally, water interferes with traditional adhesives. Great strides have been made in producing adhesives that resist water. However, this is often achieved by making the adhesive even more aggressive—certainly not ideal for ease of removal from hairy regions of the body.

The present inventor, therefore, has followed the path laid out by the highly successful "sticky" notes. These ubiquitous devices generally have a pressure-sensitive adhesive that was considered too weak for any practical use. Yet these notes temporarily stick to almost anything and can be readily removed usually without damaging the surface to which they adhere. The answer then is to select a "weak" adhesive that is strong enough to keep a thermal dressing in place but weak enough to allow relatively ready removal. These types of adhesives are best described as "tacky" adhesives. Although a small surface area of such an adhesive may not support a great load, relatively large areas of such a weak tacky adhesive can readily hold a thermal dressing in place. Whereas prior art thermal dressings employing an adhesive to attach themselves to a body part generally employ an area of adhesive smaller than the supported thermal unit, the use of tacky adhesive generally requires an adhesive area equal to or preferentially larger than the supported thermal device.

Tacky adhesives are generally very flexible and applied in relatively thick layers. They adhere by molding themselves to every irregularity of the underlying surface. Because the adhesive layers are relatively thick (usually 0.1 mm or more in thickness), they can adhere to surfaces too rough for traditional adhesives. In particular they can adhere to hairy as well as smooth regions of skin. And yet although they can adhere well to most hairy regions, they can be easily stripped off without pulling the hairs or otherwise causing pain or damage.

Figure 2A:
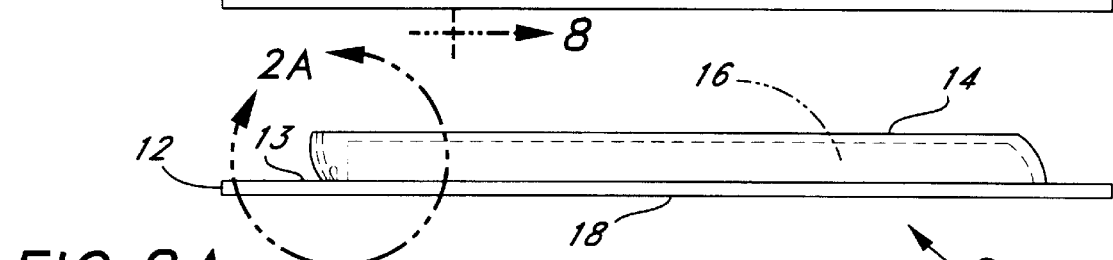
FIG. 2A is a diagram of the cold pack of FIG. 1 shown in longitudinal cross section.
Figure 3:
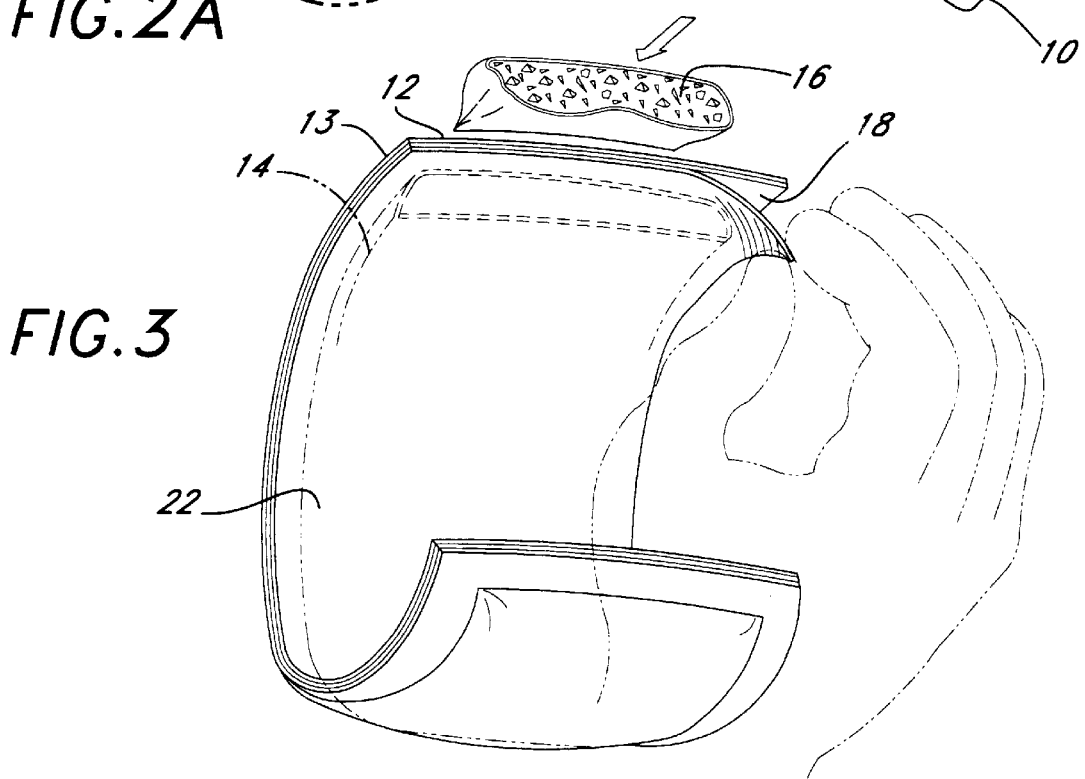
FIG. 3 shows a perspective view of the device with the protective sheet being peeled off.

The inventor has found that the optimum type of tacky adhesive for use with thermal dressings is a hydrated hydrophilic gel. The ideal gel is of sufficient molecular weight (e.g., crosslinked) so as to be insoluble or only sparingly soluble in water. The entire thermal dressing 10 is shown in FIG. 1. Here an adhesive substrate 12 carries a thermal capsule 14. In this illustration the capsule 14 is open at one end to allow the insertion of a hot or cold pack (arrow in FIG. 3). As shown in FIG. 2A, the substrate 12 bears on its lower surface a layer 18 of hydrophilic gel adhesive. This adhesive is only effective when hydrated. If allowed to dry completely, it loses most if not all of its adhesive properties. However, adhesiveness can be readily regenerated by rehydrating the gel. Therefore, the entire dressing 10 is usually sealed in a water vapor impermeable package (e.g., foil or aluminized mylar). The preferred packaging (not shown) is similar to that used to maintain sterility in most disposable medical devices.

Figure 2B:
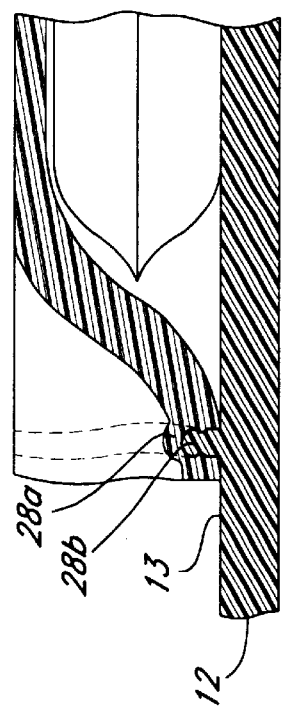
FIG. 2B is a diagram of the cold pack of FIG. 2A showing a ridge seal.
Figure 12:
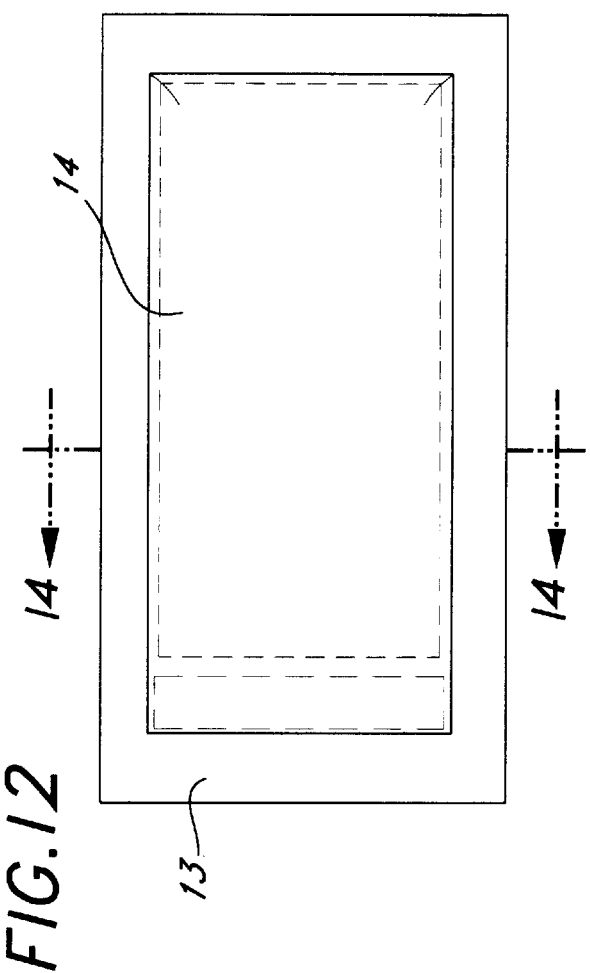
FIG. 12 is a plan viewing of a device using a hook and loop device to removably seal the thermal capsule.
Figure 13:
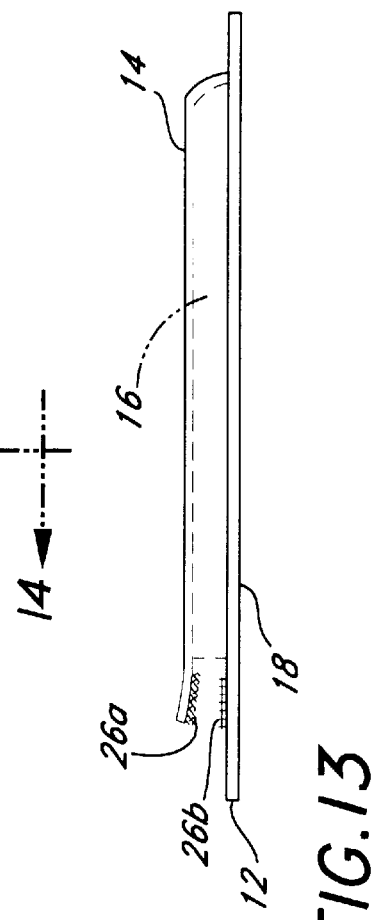
FIG. 13 is a sectional view of the device of FIG. 12 showing the hook in loop fastener.
Figure 11:
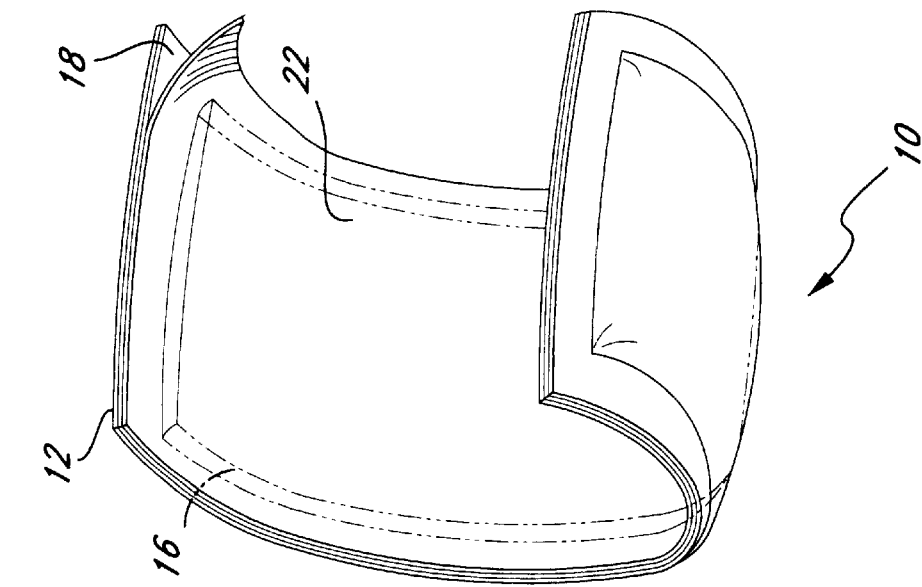
FIG. 11 shows a perspective drawing of the device having a permanently sealed thermal capsule.

FIG. 2B shows that the open pocket-like thermal capsule 14 is preferentially closed by a leak proof "ridge seal" 28a, 28b which allows the insertion and removal of a thermal pack. Alternatively, a hook in look fastener 26a, 26b can be used to removably close the thermal capsule 14 (FIGS. 12 and 13). In addition, the capsule can be permanently sealed with adhesive or a heat seal/bond as in FIG. 11).

Once the impermeable package is opened, a protective layer 22 (FIG. 3) can be stripped off to reveal the adhesive layer 18. In the figures the thermal material 16 is enclosed in an impermeable polymeric sheath 14. The thermal material can be a typical gel material that is heated or cooled prior to use. A preferred device is to provide heating or cooling through some type of phase change system. For example, a cold thermal device 16 can be provided by an ammonium nitrate cold pack wherein the local temperature is lowered by dissolution of a salt (ammonium nitrate). Similarly hot packs can be provided by chemical reaction or phase change. Although the illustrated design shows an integral thermal pack, it is also contemplated to provide the adhesive-coated substrate and backing with an integral pocket attached to the top surface (surface away from the adhesive layer 18). This way a thermal source (ice or heated gel pack) can be inserted into the pocket before or after application of the dressing 10 to the patient. With such an arrangement it is possible to renew the thermal source 16 independently of the adhesive portion of the dressing.

Figure 4:
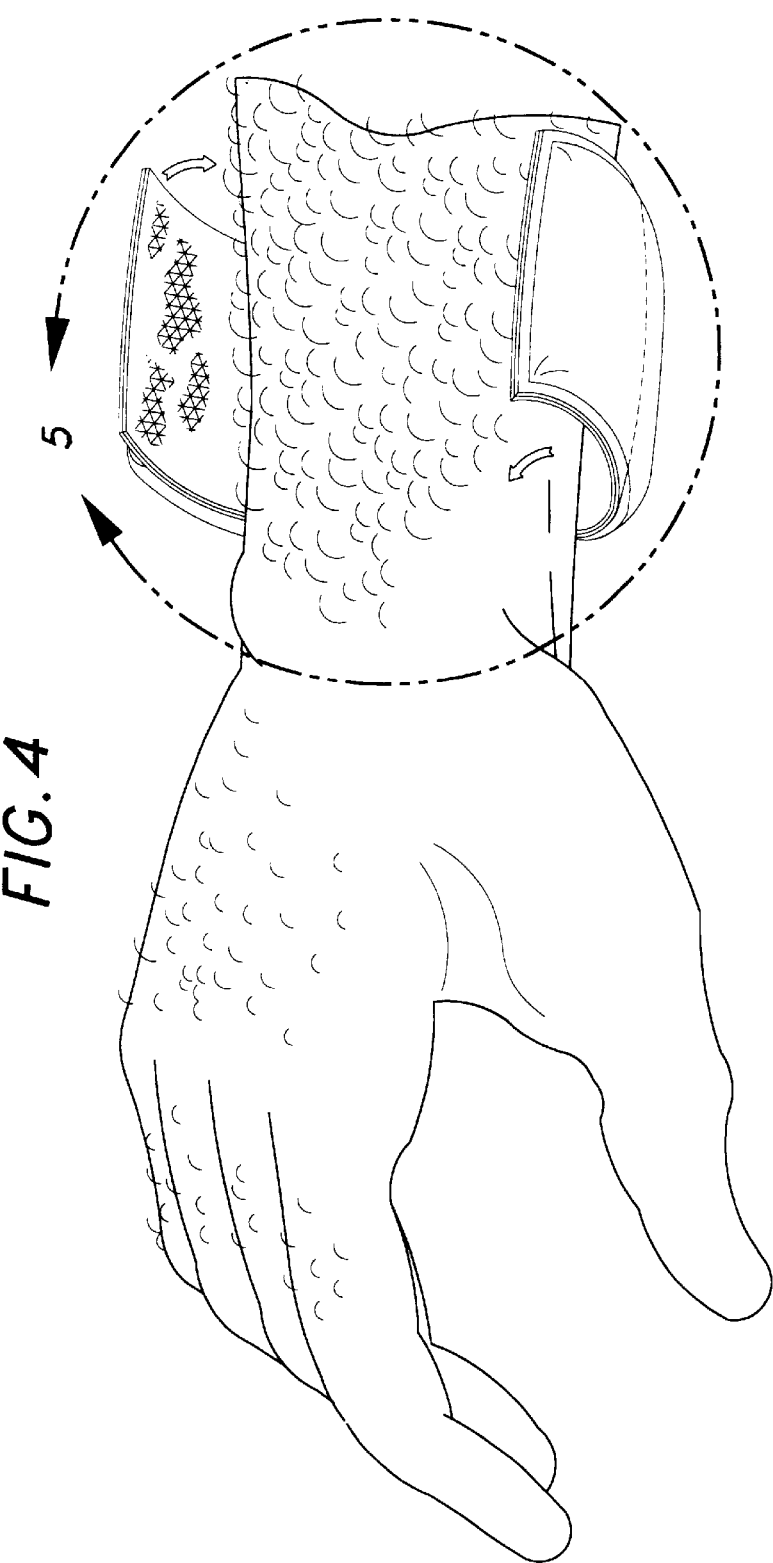
FIG. 4 is a perspective diagram of the device being placed around the wrist of a patient.
Figure 5:
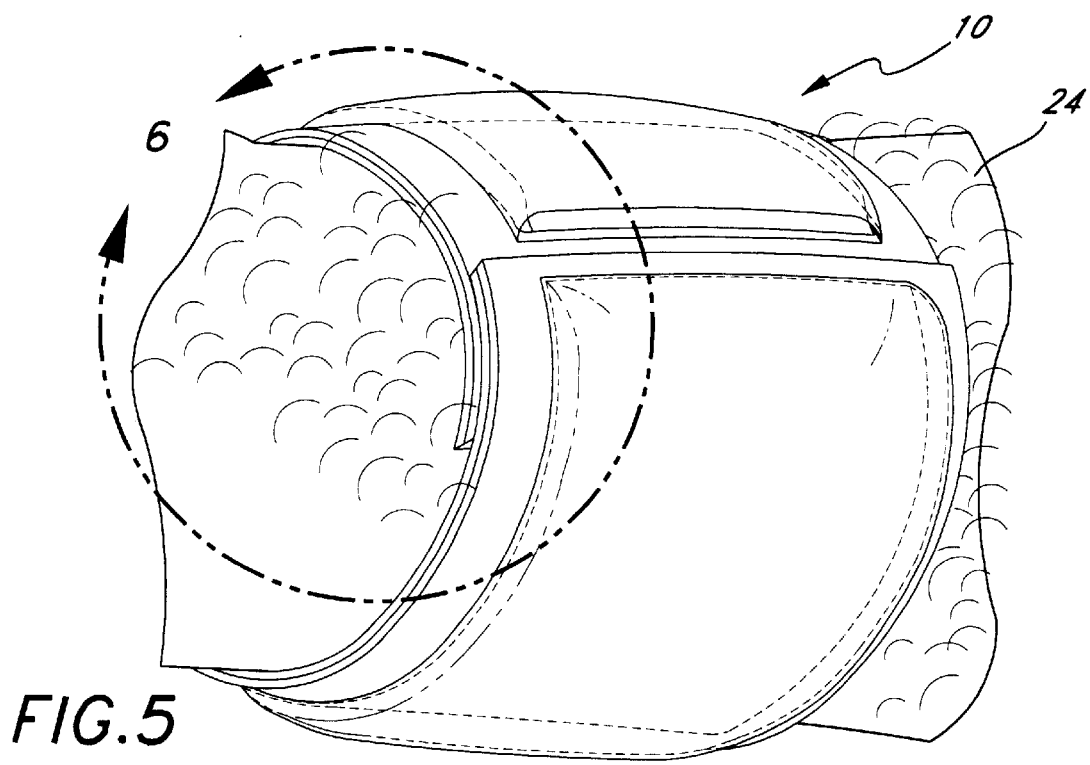
FIG. 5 is a close-up view of a portion of FIG. 4 wherein the device is attached by overlapping.
Figure 6:
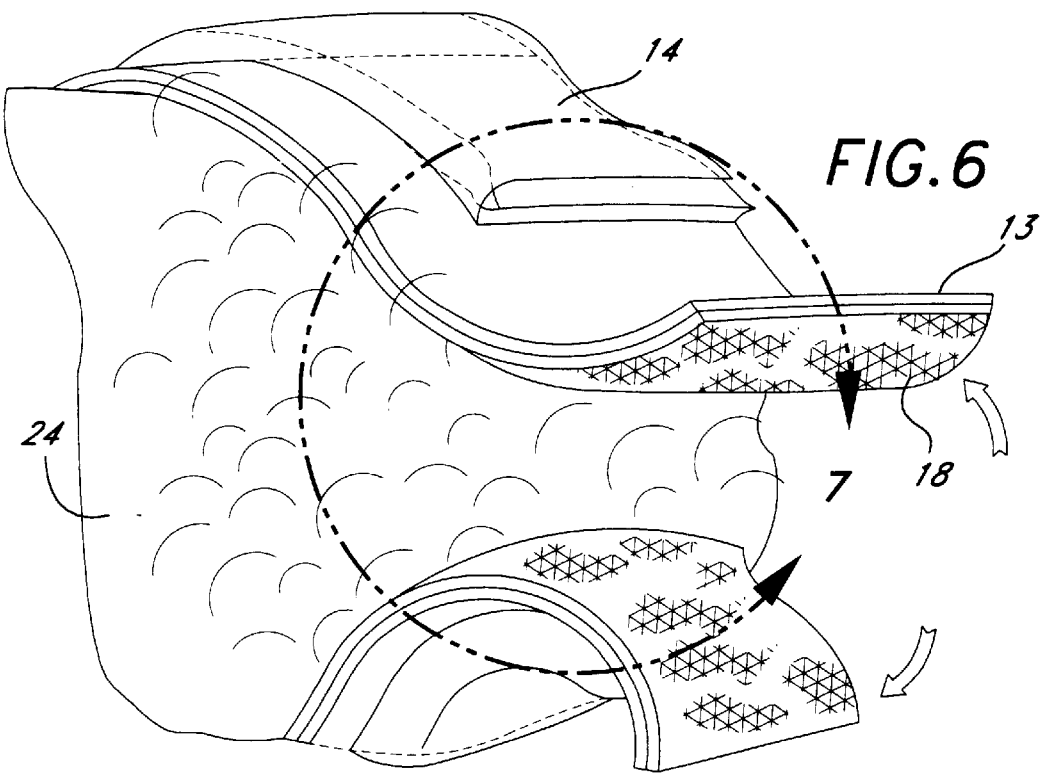
FIG. 6 shows a close-up view of the removal of the device showing the surface of the adhesive layer.
Figure 7:
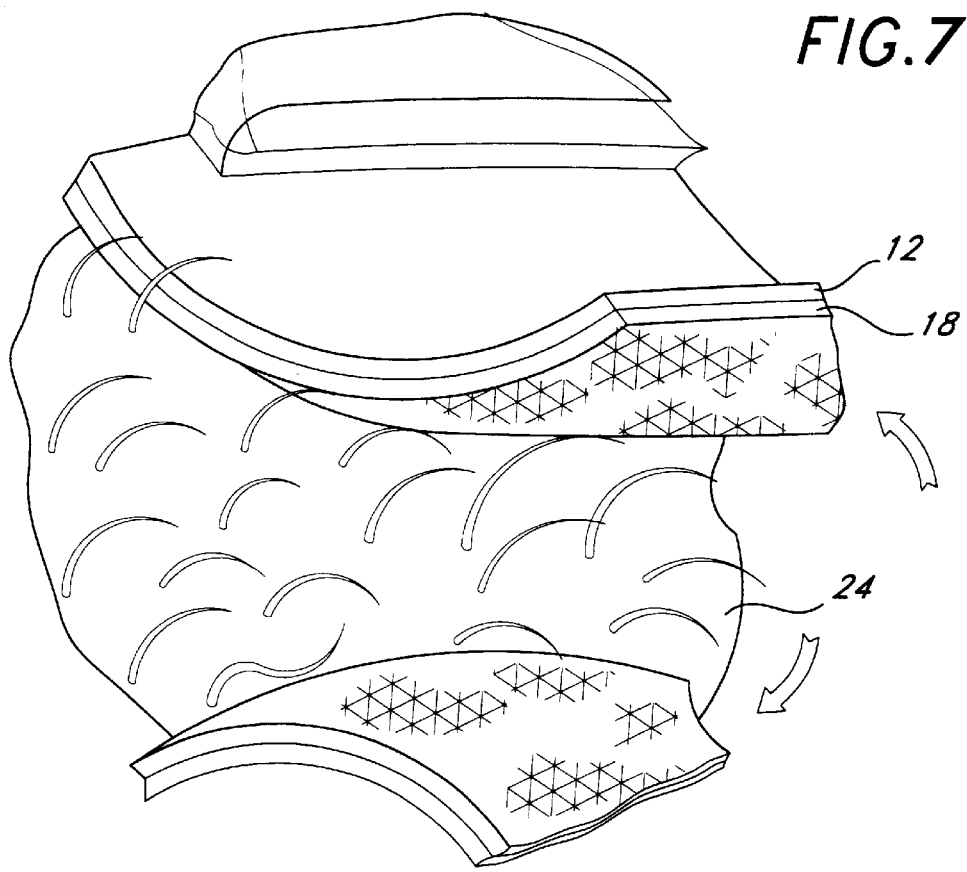
FIG. 7 is a close-up view of removal emphasizing the lack of sticking to body hair.
Figure 9:
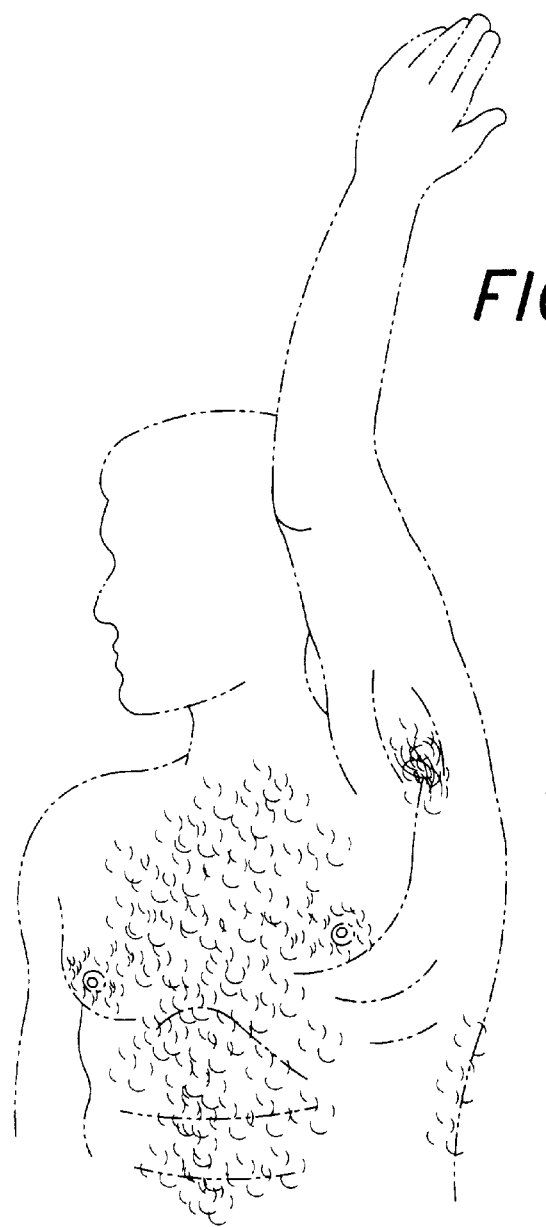
FIG. 9 shows the torso of a patient.
Figure 10:
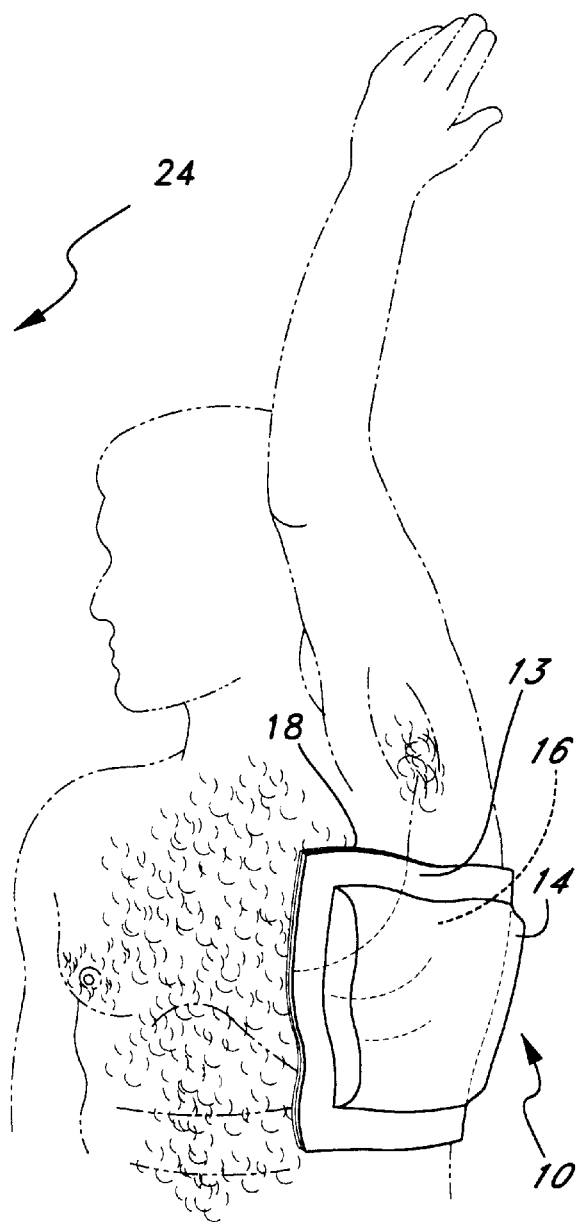
FIG. 10 shows the device adhering to the torso of FIG. 9 without wrapping entirely around a body portion.

FIG. 4 illustrates one use of the dressing 10 where it is wrapped completely around the wrist of a patient 24. This is shown in detail in FIG. 5 whereas FIG. 6 and FIG. 7 show the device 10 being removed. It should be noted that the dressing 10 adheres despite an abundance of body hair. Further, when the dressing 10 is peeled off (FIG. 7) the underlying hairs are essentially untouched. The absence of traditional elastomeric components such as latex seems responsible for this behavior. However, it should not be imagined that adhesion depends on wrapping as shown in FIG. 5. FIG. 9 and FIG. 10 show that a large thermal pack can be readily adhered to the chest of a patient to deal with bruised ribs or similar contusions. In such a case it is not possible to wrap the device 10 around a limb. Nevertheless, the hydrophilic gel provides adequate adhesion despite the presence of body hair.

Figure 8:
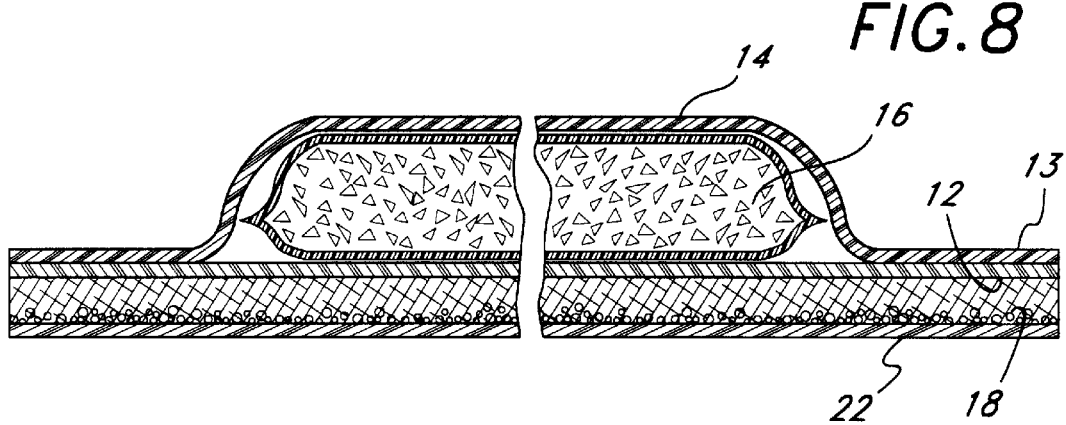
FIG. 8 shows a cross section of the device of FIG. 1 to show the internal structure.

As shown in FIG. 8, a preferred embodiment of the hydrophilic gel adhesive 18 represents a layer of gel coated on and penetrating into a porous backing 12 (in this case a felt-like non-woven fabric). An optional impermeable coating 13 can be laminated to the upper surface of the backing 12. The hydrophilic gel does not contain latex or similar elastomers and is essentially non-sticky when dry. The gel is hypoallergenic so that neither physical nor allergic damage can be caused by use of the dressing. Preferably the gel is insoluble (or only partially soluble) in water and is either coated onto the backing 12 using a non-aqueous solvent or is polymerized in place. The gel may be any of a number of carbohydrate gels such as agars or carregenan or plant gums (guar, etc.). It may also be composed from polymerized monomers such as polyacrylamide or similar acrylates. Advantageously, the coating may contain a humectant such as glycerin or propylene glycol to help maintain moisture levels and act as a plasticizer. Of course, preservatives such as disodium EDTA and methy benzoate are advantageously included. After the hydrophilic gel 18 is coated on the backing 18, the protective sheet 22 is placed over the adhesive layer 18 to prevent uncontrolled sticking, the thermal source 16 is attached and the entire dressing 19 is sealed in a moisture impermeable package to maintain hydration of the adhesive layer 18.

EXAMPLE

The preferred hydrophilic gel is made especially for the disclosed device. However, a commonly available medication called "Cool Relief" is available from Kubo Body Care. This material is a hydrophilic gel designed to dispense menthol and other "heating" medications rather like a liniment. The material is coated on a backing, and a thermal capsule can be readily attached to such backing to yield a device with properties similar to the instant invention (apart from the pronounced odor and feel of menthol and other active liniment ingredients).

The following claims are thus to be understood to include what is specifically illustrated and described above, what is conceptually equivalent, what can be obviously substituted and also what essentially incorporates the essential idea of the invention. Those skilled in the art will appreciate that various adaptations and modifications of the just-described preferred embodiment can be configured without departing from the scope of the invention. The illustrated embodiment has been set forth only for the purposes of example and that should not be taken as limiting the invention. Therefore, it is to be understood that, within the scope of the appended claims, the invention may be practiced other than as specifically described herein.

I claim:

1. An improved thermal dressing comprising:
   a permeable support;
   a layer of hydrated hydrophilic gel containing no elastomers, the layer coating and penetrating into a first surface of the permeable support to provide an adhesive for removably adhering to skin or hair without causing pain or damage when the layer is brought into contact with skin or hair; and
   a thermal source for supplying either heat or cold attached to a second surface of the permeable support so that the source can be removably attached to skin or hair of a patient by said layer of hydrophilic gel.

2. The device of claim 1, wherein the thermal source is enclosed in a thermal capsule.

3. The device of claim 2, wherein the thermal capsule has an opening for the insertion of the thermal source.

4. The device of claim 3, wherein the opening is closed by a closure selected from the group consisting of hook in loop fasteners, ridge seals, adhesive seals and heat seals.

5. An improved thermal dressing comprising:
   a permeable support;
   a layer of hydrated hydrophilic gel, the layer coating and penetrating into a first surface of the permeable support to provide an adhesive for removably adhering to skin or hair without causing pain or damage when the layer is brought into contact with skin or hair; and a thermal source for supplying either heat or cold attached to a second surface of the permeable support so that the source can be removably attached to skin or hair of a patient by said layer of hydrophilic gel.

6. The device of claim 5, wherein the thermal source is enclosed in a thermal capsule.

7. The device of claim 6, wherein the thermal capsule has an opening for the insertion of the thermal source.

8. The device of claim 7, wherein the opening is closed by a closure selected from the group consisting of hook in loop fasteners, ridge seals, adhesive seals and heat seals.

9. An improved thermal dressing comprising:

a support layer;

a layer of hydrated hydrophilic gel, the layer coating and adhering to a first surface of the support layer to provide an adhesive for removably adhering to skin or hair without causing pain or damage when the layer is brought into contact with skin or hair; and a thermal source for supplying either heat or cold attached to a second surface of the permeable support so that the source can be removably attached to skin or hair of a patient by said layer of hydrophilic gel.

10. The device of claim 9, wherein the thermal source is enclosed in a thermal capsule.

11. The device of claim 10, wherein the thermal capsule has an opening for the insertion of the thermal source.

12. The device of claim 11, wherein the opening is closed by a closure selected from the group consisting of hook in loop fasteners, ridge seals, adhesive seals and heat seals.

* * * * *